(12) United States Patent
Solomon et al.

(10) Patent No.: US 9,737,350 B2
(45) Date of Patent: Aug. 22, 2017

(54) SURGICAL SCREW AND METHOD OF PERFORMING LIGAMENT RECONSTRUCTION USING SAID SCREW

(75) Inventors: Daniel J. Solomon, Tiburon, CA (US); Matthew T. Provencher, Coronado, CA (US); Colin Gregersen, Salt Lake City, UT (US)

(73) Assignee: The United States of America as Rep. by the Secretary of the Navy, Washington, DC (US)

( * ) Notice: Subject to any disclaimer, the term of this patent is extended or adjusted under 35 U.S.C. 154(b) by 158 days.

(21) Appl. No.: 12/855,071

(22) Filed: Aug. 12, 2010

(65) Prior Publication Data
US 2011/0040339 A1    Feb. 17, 2011

Related U.S. Application Data

(60) Provisional application No. 61/233,303, filed on Aug. 12, 2009.

(51) Int. Cl.
*A61B 17/86* (2006.01)
*A61F 2/08* (2006.01)

(52) U.S. Cl.
CPC ...... *A61B 17/8695* (2013.01); *A61B 17/8605* (2013.01); *A61F 2/0811* (2013.01); *A61B 17/864* (2013.01); *A61B 17/8685* (2013.01); *A61F 2002/0835* (2013.01); *A61F 2002/0858* (2013.01); *A61F 2002/0888* (2013.01)

(58) Field of Classification Search
CPC .................................................. A61B 17/8695
USPC ................ 606/305–308, 319, 321, 322, 323
See application file for complete search history.

(56) References Cited

U.S. PATENT DOCUMENTS

| | | | |
|---|---|---|---|
| 6,524,316 B1* | 2/2003 | Nicholson et al. | 606/326 |
| 2006/0015107 A1* | 1/2006 | Sklar | A61F 2/0811 623/13.14 |
| 2006/0189991 A1* | 8/2006 | Bickley | 606/72 |

\* cited by examiner

*Primary Examiner* — David Bates
*Assistant Examiner* — Olivia C Chang
(74) *Attorney, Agent, or Firm* — Albert M Churilla; Ning Yang; Diane Tso

(57) ABSTRACT

This invention relates to a system and a method for affixing soft tissue to bones. The system for fixing soft tissue within a bone tunnel comprising a first fixation member having a proximal end and a distal end and a bore extending from said proximal end to said distal end, said first fixation member is adapted for insertion against a first portion of a soft tissue positioned within a bone tunnel, a second portion of said soft tissue emerging from said bone tunnel; a second fixation member adapted to engage said bore of said first fixation member, having means for restraining disengagement therewith and a proximal end; and a third fixation member adapted to engage said second portion of said soft tissue, having means for coupling onto said proximal end of said second fixation member and restraining disengagement therewith.

18 Claims, 5 Drawing Sheets

SURGICAL SCREW AND METHOD OF PERFORMING LIGAMENT RECONSTRUCTION USING SAID SCREW

CROSS-REFERENCE OF RELATED APPLICATIONS

Figure 1A:
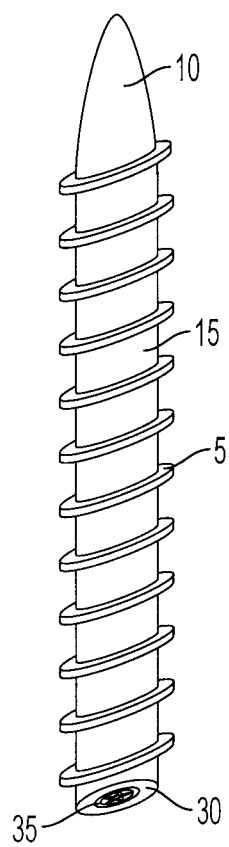

This application claims priority to provisional application 61/233,303 filed Aug. 12, 2009.

TECHNICAL FIELD

This invention relates to a surgical screw and a method for anchoring a tendon or ligament implant to bones. More specifically, this invention relates to the fixation of a ligament using said surgical screw in reconstruction surgery.

BACKGROUND

When a ligament becomes detached from a bone, surgery usually is required to reconstruct the ligament. Often, a substitute ligament or graft is secured into bone tunnels to facilitate the incorporation of the ligament and permanent attachment.

An example of this type of surgery is the reconstruction of torn knee ligaments, particularly the anterior cruciate ligament (ACL) and the posterior cruciate ligament (PCL). Surgical reconstruction is the standard of care after cruciate ligament injuries. Tears of knee ligaments can render the knee unstable leading to recurrent episodes of giving way. Reconstruction of these ligaments by using tendon grafts can result in restoration of knee stability and function. To perform a ligament reconstruction, remnants of the torn ligament are removed. Next, bone tunnels are drilled in the femur and tibia bones at the attachment site for the ligament to be reconstructed. A tissue graft is then spanned between the tunnels with the graft ends buried in the bone tunnels. Finally, the graft is tensioned and attached securely to the bone tunnels. The graft then undergoes a slow process of healing, which creates a firm attachment of the graft to bone, and establishes a new blood supply for the graft. Over a period of 6-18 months, the graft remodels to become living tissue, which can resist abnormal motions of the knee that would result in giving way.

The fixation of the graft to the bones is of paramount importance in this type of surgeries as any loosening of the graft can result in failure to restore knee stability. Furthermore, early knee motion and exercises which help the patient to recover quickly from surgery can place significant stress on the graft fixation. Adequate stability of graft fixation must be achieved to allow the patient to safely benefit from the effects of early rehabilitation.

Several types of tissue grafts are available for use in knee ligament reconstruction. Each type of graft has certain advantages and disadvantages. The use of autologous hamstring tendons in knee ligament reconstruction has grown in popularity because this graft causes very minimal morbidity to harvest, does not disrupt the extensor mechanism, creates a very strong soft tissue graft and does not expose a patient to the risks of using cadaver tissue. However, fixation of hamstring grafts to the proximal tibial bone tunnel remains a weak link in successful use of the hamstring tendons. The proximal tibia often contains soft bone providing a weak substrate for implant fixation. A second problem is that the tibia is only covered by a thin layer of soft tissue and a prominent implant can often be palpated beneath the skin causing pain. Other types of soft tissue grafts, both of autologous and cadaver tissue, including achilles tendon, quadriceps tendon, fascia lata and palmaris longus tendon are used in certain situations to reconstruct the ligaments. Again the weak link of fixation to the bone tunnel remains a problem.

A number of devices are known in the prior art for fixation of soft tissue grafts to bones. However, as it will become evident, each of these devices possesses problems that limit their successful use.

The first class of devices for soft tissue to bone fixation is suture anchor, such as the anchor illustrated by U.S. Pat. No. 5,472,452. In his description, Trott discloses a bone anchor which can be placed in a small bone hole, and then serves as the attachment site for soft tissues which are sutured to the bone. Similar type devices are further disclosed by Lee and Sander in U.S. Pat. No. 5,480,403 and by Hayhurst in U.S. Pat. No. 5,601,557. A variation on this device is disclosed by Ross, Snyder, Marchand in U.S. Pat. No. 5,246,441 where a tack is used to secure soft tissues against the bone as it is driven into a small bone hole. These devices do not provide sufficient holding strength suitable for fixation of knee ligament grafts.

A second class of fixation devices is illustrated by U.S. Pat. Nos. 4,454,875 and 4,570,623 where metal staples with spikes on the underside are seen securing ligament tissue to bone. These devices are undesirable in that they have less than ideal fixation strength. The devices are often difficult to use and reposition may cause damage to the bone. They may also be palpable beneath the skin causing pain and necessitating a second operation for their removal.

A third class of fixation device is the interference screw. An example of this type of implant is the RCI® screw marketed by Smith-Nephew Endoscopy Corp (Boston, Mass.). The RCI® screw has blunt threads to avoid damage to a soft tissue graft. This screw is threaded into a bone tunnel alongside of the strands of a soft tissue graft. The screw holds the graft in place by compressing the soft tissue graft against the sides of the bone tunnel. Unfortunately, interference screws have poor fixation strength against soft tissue grafts.

A forth class of fixation device uses a screw-washer combination design. This device consists of a standard bone screw and a washer, which is placed distal to the bone tunnel. The screw may be tightened down over a soft tissue graft capturing it against the tibia or can act as an anchor around which to tie sutures. U.S. Pat. No. 6,123,711 by Winters et al. discloses such a fixation system with the screw-washer design. However, the screw-washer assembly is often prominent, causing pain and requiring a second operation for implant removal. The tack described by Winters et al. is only inserted into the top portion of the outside screw, resulting in weak graft fixation leaving concerns of graft slippage. In addition, the tack is retained onto the screw by the barb head of the tack, surgeons are not able to adjust the tightness of compression exerted by the washer.

A fifth class of fixation device is a button over which sutures may be tied. Fixation strength of this type of device is limited by the strength of the sutures. In some cases the button may be too prominent and requires post-surgery removal.

Other implants such as the Endobutton® of Smith-Nephew Endoscopy Corp. (Boston, Mass.) and various types of threaded pins over which the graft is wrapped are only applicable to fixation of the tendon graft on the femoral side of an ACL reconstruction and thus do not provide a solution to the weak link on the tibial side.

The disadvantages of the available methods of soft tissue fixation can be summarized as:
A. poor fixation strength allowing slippage of the graft during early rehabilitation;
B. limited bone to tendon interface for healing;
C. prominence of the implant which may cause pain;
D. difficult to adjust fixation;
E. requirement of second surgery for implant removal;
F. damage to bone by implant;
G. implants not amenable to tibia sided graft fixation.

SUMMARY OF INVENTION

The present invention provides a system and method for affixing soft tissue to bones. It further provides a system that has an element for securing the soft tissue piece within a bone tunnel and another element for securing a second portion of the soft tissue against the outside of the bone tunnel.

An embodiment of the system is for fixing soft tissue within a bone tunnel, which comprising a first fixation member having a proximal end and a distal end and a bore. The first fixation member is adapted for insertion upon a first portion of soft tissue positioned within a bone tunnel. A second portion of the soft tissue is positioned to emerge from the bone tunnel. The proximal end of the bore may be pre-threaded for mating with a second fixation member. The second fixation member may include a distal post portion threaded for mating with the proximal portion of the first fixation member. The second fixation member may be further adapted to be self-tapping, which creates threads inside the bore of the first fixation member as it is rationally driving into the first fixation member. A third fixation member may be adapted to engage said second portion of said soft tissue, and having means for coupling onto said proximal end of said second fixation member, and thus restraining it from disengagement from the first fixation member.

In a subembodiment, the first fixation member is a screw type device, having blunt thread adapted to be inserted into the bone tunnel, pressing the graft inside against the surface of the tunnel. The second fixation member is a self-tapping screw which advances when turned, while creating its own threads inside the bore of the first fixation member. As the second fixation member advances inside the bore of the first fixation member, uniform expansion is created along the length of the first fixation member, further compressed the graft inside the bone tunnel against the internal wall of the tunnel. The third fixation member may be a washer, which may contain barbs underneath, and fully engage the portion of soft tissue that is hanging outside the bone tunnel to the bone surface.

In another subembodiment, the first fixation member may contain a recess to allow the washer to seat flush with the top of the outer screw. The washer is also indented to allow the inert screw to seat flush inside the washer. Thus, reducing the size of the fixation member extending outside the bone tunnel, and reducing patient discomfort.

DETAILED DESCRIPTION OF THE DRAWINGS

Figure 1B:
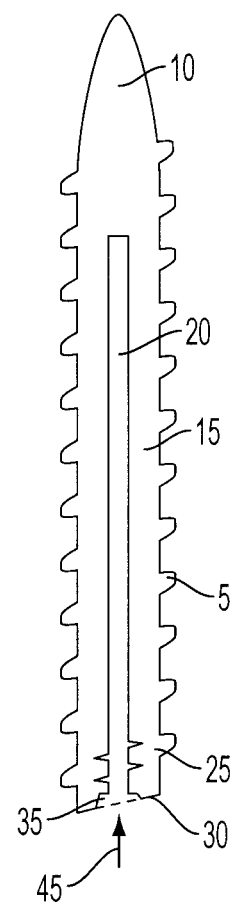
Figure 1C:
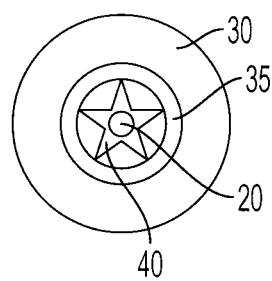
Figure 2A:
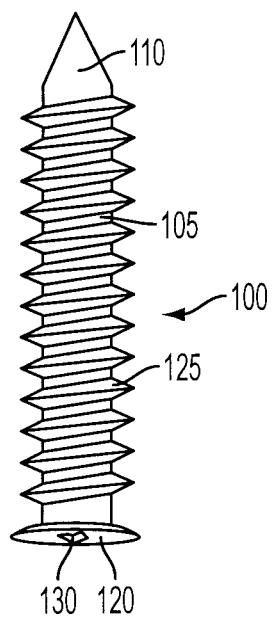
Figure 2B:
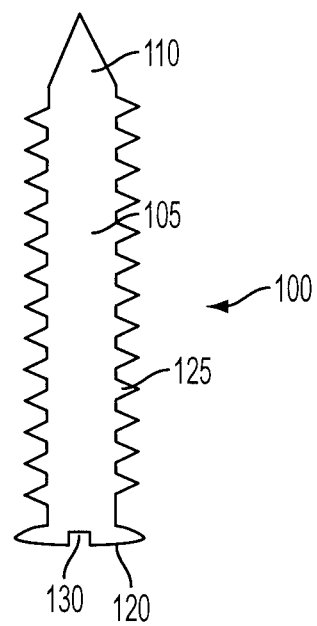
Figure 2C:
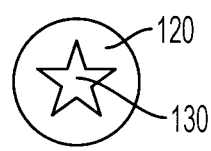
Figure 3A:
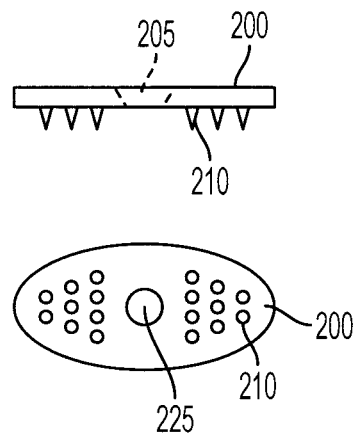
Figure 3B:
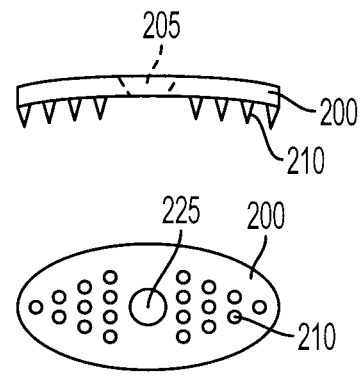
Figure 3C:
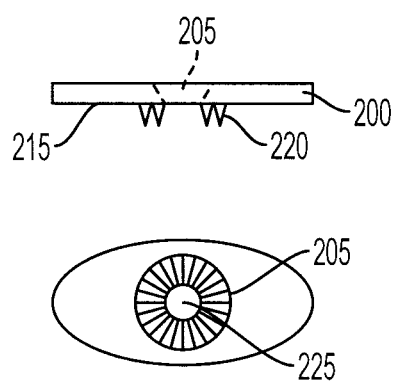
Figure 4:
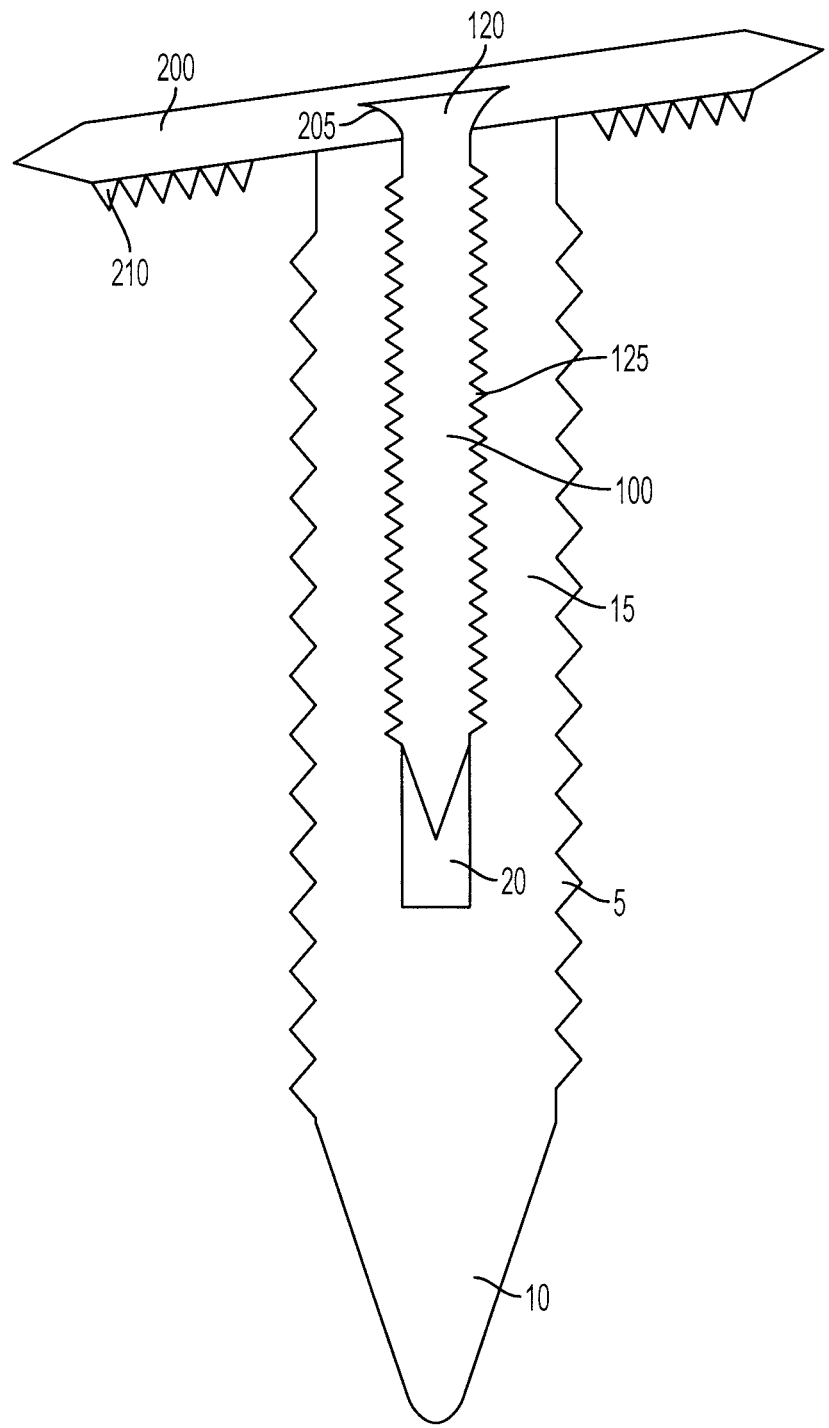
Figure 5:
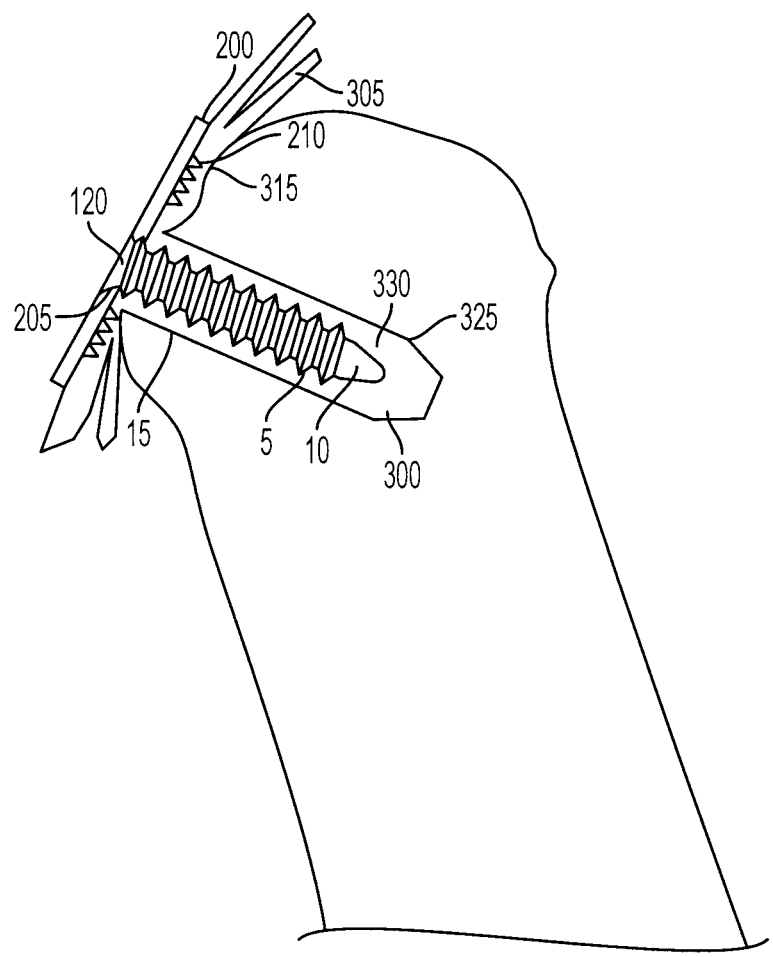

FIG. 1a shows a side view of an embodiment of the first fixation member.
FIG. 1b shows a cross-sectional view of an embodiment of the first fixation member.
FIG. 1c shows a top view of the proximal end of an embodiment of the first fixation member.
FIG. 2a shows a side view of an embodiment of the second fixation member.
FIG. 2b shows a cross-sectional view of an embodiment of the second fixation member.
FIG. 2c shows a top view of the proximal end of an embodiment of the second fixation member.
FIG. 3a shows an embodiment of the third fixation member.
FIG. 3b shows an embodiment of the third fixation member.
FIG. 3c shows an embodiment of the third fixation member.
FIG. 4 shows a cross-sectional view of an embodiment of an assembled fixation device.
FIG. 5 shows the cross-sectional view of the assembled fixation device stabilizing a soft tissue graft within a bone tunnel.

DETAILED DESCRIPTION OF THE INVENTION

The embodiments of the invention, both as to the device and method of operation, will be better understood from the following description used in conjunction with the accompanying drawing. It is to be expressly understood that the drawing is for the purpose of illustration and description, and is not intended as a definition that limits the invention.

An embodiment of the present invention is a system for fixing soft tissue within a bone tunnel, comprising: a first fixation member having a bore extending from its proximal end to about its distal end and adapted for insertion against a portion of a soft tissue positioned within a bone tunnel, a second fixation member adapted to engage the bore of the first fixation member, and having means for restraining disengagement therewith, and a third fixation member coupled onto the second fixation member and adapted to engage a portion of the same soft tissue, which emerging from said bone tunnel. The fixation members may be made of biocompatible metal or metal alloys such as titanium. Alternatively, one or all three fixation member may be made of a biodegradable material to eliminate the need of future removal, such as the materials described in U.S. Pat. No. 4,356,572, U.S. Pat. No. 5,522,895, U.S. Pat. No. 4,655,777 and U.S. Pat. No. 5,085,861.

Biodegradable. The term "biodegradable" is intended for the purposes of the present invention, to include bioresorbable, bioabsorbable, biodegradable, and bioerodible materials that are well known to those of ordinary skill in the art and are described in Biomaterials Science—An Introduction to Materials in Medicine, edited by Ratner, B. D. et al., Academic Press, (1996), and include for example, the following materials: chitosan; isomorphic ploy(hexamethylene co-trans-1,4-cyclohexane dimethylene oxalates); poly(glycolic acid); copolymers of poly(glycolic acid) and poly (lactic acid); polydioxanone; poly(latic acid); PLLA with Tricalcium phosphate, or PEEK, or polymers having a back-bone structure selected from the group consisting of: polyanhydrides, polyphophazenes, polyphosphonates, polyamides, and polyiminocarbonates; polyhydroxybutyrate; polyhydroxyvalerate; copolymers of polyhydroxybutyrate and polyhydroxylerate; polycaprolactone; polydioxanone; poly(.gamma.-ethyl glutamate); poly(DTH iminocarbonate); poly(Bisphenol A iminocarbonate); poly(DETOSU-1,6 HD-t-CDM ortho ester); poly(Sebacic acid-hexadecandioic acid anhydride); poly(ortho esters); poly(amino acids); and PLOA. Such polymers may optionally include one or more pharmaceutically active agents for controlled release applications, such agents including for example: osteoinductive factors including for example bone morphogenic protein, antiobiotics, and anti-inflammatory agents.

Biocompatible. By the term "biocompatible" is intended for the purposes of the present invention, any material which when implanted in a patient does not provoke an adverse response in the patient. A suitable biocompatible material when introduced into a patient is not toxic or injurious to that patient, or does not cause immunological rejection.

FIGS. 1A, 1B and 1C illustrate an embodiment of a first fixation member (15). In this embodiment, the first fixation member may be a screw-type device (15) ("outer screw") comprising a blunt distal end (10) and helical protrusions with a rounded edge (5) along its body, extending from the distal end (10) to the proximal end (30). The blunt distal end (10) and rounded edge (5) minimize damage to the graft tissue. An embodiment of the outer screw (15) may be generally cylindrical in shape, 20-35 mm in length and 7-12 mm in diameter. The outer screw (15) may gradually decrease in diameter near its distal end to enable easy insertion into the bone tunnel. The center of the outer screw may be cannulated creating a bore (20) extending from its proximal end (30) to its distal end (10), allowing passage of a guiding wire during surgery. The bore (20) of the outer screw (15) may be pre-threaded (25) at least partially from the proximal end. These threads have pitches matching the threads of a second fixation member (100) ("inner screw"). They may help to center the second fixation member inside the outer screw during assembly as it advances inside the bore. The proximal end (30) of the outer screw (15) may be cut at an angle (45) of 55 to 60 degrees to the vertical axis, allowing a good conformation to the tibial cortex surface after insertion into the bone tunnel. The proximal end (30) of the outer screw (15) may contain a recess (35) dimensioned to receive a portion of the third fixation member (200) ("washer") or a portion of the inner screw (100), allowing them to seat flush within the proximal end of the outer screw (15) when assembled. Tighter assembly reduces the size of fixation system extending outside the bone tunnel and thus minimizes patient discomfort. The proximal end of the outer screw may also contain a socket (40) for a screw driver, which allows the outer screw to be driven into the bone tunnel against graft strands.

FIGS. 2A, 2B and 2C show an embodiment of the second fixation member, which may be a screw type device ("inner screw"). The inner screw (100) may be made of a harder material than the outer screw allowing it to cut into the bore of the outer screw creating threads as it advances through the bore, such as a self-tapping screw. An embodiment of the inner screw may be 15-30 mm in length and has a sharp distal end (110), a generally cylindrical post body (105) and a proximal head. The post body is at least 3.5 mm in diameter and have helical protrusions (125) extending along its length. The proximal head of the inner screw (120) has a diameter larger than the post and may contain a screw driver socket (130) allowing the inner screw to be driven inside the outside screw using a screw driver (FIG. 2b).

FIG. 3a-3c illustrate various embodiments of a third fixation member (200), a "washer". The washer may be flat (FIG. 3a) or arched (FIG. 3b) and has a center bore (225) dimensioned to allow the insertion of the post of inner screw but not proximal head of the inner screw. The washer may also contain a recess (205) dimensioned to receive the proximal head (120) of the inner screw and allowing it to seat flush within the washer. This embodiment reduces patient discomfort by minimizing the portion of fixation device protruding from the bone tunnel. The washer (200) may have multiple barbs (210) protruding from its distal surface (FIG. 3a and FIG. 3b) designed to compress the soft tissue residing outside the bone tunnel against the bone surface. The barbs may have a rounded tip to reduce damages to the soft tissue. The washer may also has a smooth distal surface (215) and a circular collar (220) around the bore, which is designed to secure suture between the washer and the outer screw when assembled (FIG. 3c). The washer may be of any shape, such as round (FIG. 3d) or football (FIG. 3e) shaped, and is generally 14 to 18 mm in diameter.

FIG. 4 shows a cross-sectional view of an embodiment of an assembled fixation device. The self-tapping inner screw (100) is driven inside the outer screw (15) causing the outer screw to uniformly expand along its length and is refrained froth disengagement from the outer screw by their mating thread pitches. The washer (200) is coupled onto the proximal end of the inner screw (100) and is refrained from disengagement by the proximal head (120) of the inner screw. The inner screw (100) may seat flush inside the recess (205) of the washer (200). It may engage the inner screw (100) with 20 to 30 degree of freedom of operation. If the washer of FIG. 3c is used, the proximal end of the outside screw will also contains a recess to receive the collar of the washer allowing it to sit flush inside the outside screw.

In an embodiment, the third fixation member may be eliminated. Barbs were added under the proximal head of the second fixation member around the post body, which compresses the soft tissue residing outside the bone tunnel against the bone surface when assembled.

Another embodiment of the present invention is a method for affixing soft tissue within a bone tunnel comprising:
 a. positioning a piece of soft tissue in a bone tunnel such that a portion thereof resides within the bone tunnel and a second portion of said soft tissue reside outside the bone tunnel;
 b. positioning a first fixation member upon the piece of soft tissue within the bone tunnel;
 c. coupling a third fixation member onto a second fixation member;
 d. restraining disengagement between the first and the third fixation members by advancing a distal portion of said second fixation member within the bore of the first fixation member through the proximal end of the first fixation member; and
 e. pressing said second portion of said soft tissue against bone surface outside said bone tunnel via the third fixation member.

The inventive fixation system and method may be used in most surgical procedures requiring affixation of soft tissue to bone, such as in anterior cruciate ligament (ACL) and the posterior cruciate ligament (PCL) reconstruction surgeries.

For example, in an ACL reconstruction surgery, a new ACL graft must be affixed to the tibia and femur to replace the damaged ACL. The replacement ACL may be a tendon with a small portion of bone on either end such as a patellar tendon autograft or a strong new ACL formed by looped small tendons such as semitendinosus-gracilis (hamstring) tendons, or donated achilles tendon.

First, small tunnels (300) are drilled into the tibia and femur as shown in FIG. 5. A replacement ACL is placed into the bone tunnel following routine surgical procedure, leaving a portion of the graft outside the tunnel (305). Once the replacement ACL graft is inserted into the bone tunnel, the outer screw is inserted into the bone tunnel using a screw driver or guide wire, pressing the ACL graft against the wall of the bone tunnel (325). The outer screw (15) may be positioned so its angled proximal end levels with the bone surface (315) around the bone tunnel (300), making it less palpable beneath the skin and reduce patient discomfort. A washer (200) is coupled onto the inner screw and is refrained from disengagement by the larger proximal head (120) of the inner screw. The sharp distal end of the inner screw is inserted into the outer screw and advancing through the bore in a rotational movement driven by a screw driver. The pre-threaded portion of the outer screw can serve as guide trail, which ensures that the inner screw moves in the center of the bore. As the inner screw advance inside the bore, addition threads are cut into the outer screw and causing it to slightly expand. The radial uniform expansions along the outer screw further compresses the soft tissue inside bone tunnel (330) against the tunnel wall (325), which prevents tissue slippage. When fully assembled, the washer will press soft tissue outside bone tunnel (305) against the bone surface surrounding the tunnel (315) and further prevents graft slippage.

Another embodiment of the method for affixing soft tissue using only a first fixation member and second fixation member comprising:

a. positioning a piece of soft tissue inside a bone tunnel such that a portion thereof resides within the bone tunnel and a second portion of said soft tissue reside outside the bone tunnel;

b. positioning a first fixation member upon the piece of soft tissue within the bone tunnel;

c. advancing a distal portion of said second fixation member within the first fixation member through a proximal end of the first fixation member; and d. pressing said second portion of said soft tissue against bone surface outside said bone tunnel.

Example 1: Biomechanical Testing of a Prototype Fixation System

Methods:

A total of 26 porcine tibiae with bone mineral density obtained by quantitative CT were randomized to human tibialis anterior tendon fixation with Delta Screw (8), Intrafix (8), and Tritis (8) devices. Due to a limited number of prototypes, only two additional specimens were tested using the prototype fixation devices. The slippage for each specimen was evaluated during cyclical loading (10 to 250 N at 1 Hz for 500 cycles) followed by stiffness and ultimate strength determination in a load to failure test.

Results:

The mean slippage displacement measured after 500 cycles was similar for Delta Screw (1.42 mm±0.43); Intrafix (1.16 mm±0.32); and the prototype (1.61 mm±0.01). The Tritis implant demonstrated a statistically larger displacement (5.95 mm±3.86, p<0.001). More specifically, cyclical loading displacements were similar after 100 and 250 cycles, with the Tritis device exhibiting the largest slippage during the first 250 cycles (4.53 mm±2.74, p<0.00000), versus Delta (1.19 mm±0.41); Intrafix (0.94 mm±0.28); and prototype (0.80 mm±0.01).

The mean ultimate strength for the devices was Delta (727.5 N±140.9), Intrafix (712.8 N±235.0), and Tritis (467.6 N±98.5, p<0.000). Prototype demonstrated the highest ultimate strength (797.7N±32.6).

TABLE 1

BIOMECHANICAL TESTING OF FIXATION DEVICES

|  | Mean Slippage Displacement (500 cycles) | Cyclical Loading Displacement (250 cycles) | Mean Ultimate Strength |
| --- | --- | --- | --- |
| Delta | 1.42 mm ± 0.43 | 1.19 mm ± 0.41 | 727.5 N ± 140.9 |
| Intrafix | 1.16 mm ± 0.32 | 0.94 mm ± 0.28 | 712.8 N ± 235.0 |
| Tritis | 5.95 mm ± 3.86 | 4.53 mm ± 2.74 | 467.6 N ± 98.5 |
| Prototype | 1.61 mm ± 0.01 | 0.80 mm ± 0.01 | 797.7 N ± 32.6 |

Conclusions:

In the porcine model with human tibialis tendon graft, the Delta Screw, Intrafix, and prototype devices displayed superior cyclical loading, and ultimate failure versus the Tritis device. The present invention offered the best ultimate strength compared to the three other commonly used implants.

What is claimed is:

1. A system for fixing soft tissue within a bone tunnel comprising:

a. a first fixation member having a proximal end and a distal end and an axial bore extending from said proximal end to said distal end, said first fixation member is adapted to compress a first portion of a soft tissue positioned within a bone tunnel against the inside surface of said bone tunnel, a second portion of said soft tissue emerging from said bone tunnel;

b. a second fixation member adapted to advance along said axial bore from the proximal end to distal end of said first fixation member causing a uniform radial expansion along the length of the first fixation member, and is restrained from disengagement therewith; wherein said second fixation member has a proximal end with screw driver socket and a closed distal; and c. a third fixation member adapted to engage said second portion of said soft tissue, which is coupled to said proximal end of said second fixation member and restrained from disengagement therewith.

2. The fixation system of claim 1, wherein said first fixation member is a screw-type member comprising:

a. a blunt distal end; and b. a helical protrusion with rounded edge along said first fixation member between said distal end and said proximal end.

3. The fixation system of claim 1, wherein said bore is pre-threaded at least partially from said proximal end of first fixation member.

4. The fixation system of claim 3, wherein at least a quarter length of said bore is pre-threaded from said proximal end.

5. The fixation system of claim 1, wherein said proximal end of said first fixation member is cut at an angle.

6. The fixation system of claim 5, wherein said angle is approximately 33-35 degrees to an axial of the first fixation member.

7. The fixation system of claim 1, wherein said second fixation member comprising a. a distal post; and b. a proximal end having a diameter greater than a diameter of said post portion.

8. The fixation system of claim 7, wherein said first fixation member and said second fixation member is restraint from disengagement by traction.

9. The fixation system of claim 7, wherein said second fixation member is a self-tapping screw.

10. The fixation system of claim 9, wherein a helical groove is created along said bore by advancing said self-tapping screw through said bore from said proximal end towards distal end of said first fixation member.

11. The fixation system of claim 7, wherein said proximal end of said second fixation member have means for being driven by a driver.

12. The fixation system of claim 7, wherein said third fixation member is coupled onto the second fixation member at 1-30 degrees of freedom when said second fixation member is engaged with said first fixation member.

13. The fixation system of claim 7, wherein said third fixation member is a washer having a proximal face and a distal face, dimensioned to be larger than said bone tunnel and having a hole extending from said proximal face through to said distal face, wherein said hole is dimensioned for free rotation about said distal post of the second fixation member, and for retention by said head portion therebeneath.

14. The fixation system of claim 13, wherein said distal face of said washer is smooth.

15. The fixation system of claim 13, wherein said distal face of said washer has a plurality of barbs extending generally distalward for engaging and restraining a movement of said soft tissue.

16. The fixation system of claim 13, wherein said proximal face of said washer has an indentation dimensioned to receive said proximal head of said second fixation member.

17. The fixation system of claim 13, wherein a horizontal cross-section of said washer is generally round, square or oval.

18. The fixation system of claim 13, wherein said washer is flat or arched up to 5 degrees.

* * * * *